(12) United States Patent
Cho et al.

(10) Patent No.: US 8,706,731 B2
(45) Date of Patent: Apr. 22, 2014

(54) SYSTEM AND METHOD FOR PROVIDING HEALTHCARE PROGRAM SERVICE BASED ON VITAL SIGNALS AND CONDITION INFORMATION

(75) Inventors: Chul-Ho Cho, Seongnam-si (KR); Dong-Soo Han, Daejeon (KR); Jae-Geol Cho, Yongin-si (KR); Sun-Tae Jung, Yongin-si (KR); Min-Kyu Lee, Daejeon (KR); Ji-Soo Song, Daejeon (KR)

(73) Assignees: Samsung Electronics Co., Ltd., Samsung-ro, Yeongtong-gu, Suwon-si, Gyeonggi-do; Information & Communications University, Research & Industrial Cooperation Group, Munji-dong, Yuseong-gu, Daegu (KR)

( * ) Notice: Subject to any disclaimer, the term of this patent is extended or adjusted under 35 U.S.C. 154(b) by 788 days.

(21) Appl. No.: 12/207,732

(22) Filed: Sep. 10, 2008

(65) Prior Publication Data

US 2009/0070378 A1 Mar. 12, 2009

(30) Foreign Application Priority Data

Sep. 11, 2007 (KR) ........................ 10-2007-0092081

(51) Int. Cl.
*G06F 17/30* (2006.01)
(52) U.S. Cl.
USPC ............ 707/737; 707/741; 707/748; 707/754
(58) Field of Classification Search
None
See application file for complete search history.

(56) References Cited

U.S. PATENT DOCUMENTS

| | | | | |
|---|---|---|---|---|
| 6,151,581 | A * | 11/2000 | Kraftson et al. | 705/3 |
| 7,899,687 | B2 * | 3/2011 | Morris | 705/3 |
| 2002/0087361 | A1 * | 7/2002 | Benigno et al. | 705/3 |
| 2003/0033122 | A1 * | 2/2003 | Dempsey et al. | 702/189 |
| 2003/0109860 | A1 * | 6/2003 | Black | 606/10 |
| 2003/0153818 | A1 * | 8/2003 | Bocionek et al. | 600/300 |
| 2003/0182249 | A1 * | 9/2003 | Buczak | 706/15 |
| 2004/0068552 | A1 * | 4/2004 | Kotz et al. | 709/218 |
| 2004/0153373 | A1 * | 8/2004 | Song et al. | 705/26 |
| 2005/0021370 | A1 * | 1/2005 | Riff et al. | 705/2 |
| 2005/0049464 | A1 * | 3/2005 | Lassers et al. | 600/300 |
| 2005/0060344 | A1 * | 3/2005 | Pawlick | 707/102 |

(Continued)

FOREIGN PATENT DOCUMENTS

| | | |
|---|---|---|
| KR | 10-2002-0007717 A | 1/2002 |
| KR | 10-2003-0039333 A | 5/2003 |
| KR | 10-0727770 B1 | 6/2007 |

*Primary Examiner* — Mohammad S Rostami
(74) *Attorney, Agent, or Firm* — Cha & Reiter, LLC (57) ABSTRACT

A method for providing a healthcare program service over a wireless communication network includes receiving vital signals for a condition from measurement devices transmitted from multiple users and grouping the received vital signals, registering by a plurality of service providers corresponding healthcare programs classified by particular diseases, providing a healthcare program service to the multiple users, receiving feedback of use satisfaction for the healthcare programs from each user, counting the number of uses and gathering utilization information for each of the healthcare programs. The method further includes searching for a corresponding group of users using each healthcare program, adding up the user satisfactions and utilizations, databasing the results and upon receipt of vital signals for a condition from a particular user, comparing against similar signals and recommending a preferred healthcare program for a corresponding user group having vital signals for the condition.

20 Claims, 5 Drawing Sheets

(56) References Cited

U.S. PATENT DOCUMENTS

| | | | |
|---|---|---|---|
| 2006/0015369 A1* | 1/2006 | Bachus et al. | 705/2 |
| 2006/0020614 A1* | 1/2006 | Kolawa et al. | 707/100 |
| 2006/0259329 A1* | 11/2006 | Kline | 705/3 |
| 2007/0078355 A1* | 4/2007 | Matsumura et al. | 600/509 |
| 2007/0106672 A1* | 5/2007 | Sighart et al. | 707/10 |
| 2007/0149862 A1* | 6/2007 | Pipke | 600/301 |
| 2007/0218447 A1* | 9/2007 | Chavan | 434/350 |
| 2007/0239486 A1* | 10/2007 | Gordon | 705/2 |
| 2008/0004904 A1* | 1/2008 | Tran | 705/2 |
| 2008/0103405 A1* | 5/2008 | Banet et al. | 600/523 |
| 2008/0147635 A1* | 6/2008 | Im, II | 707/5 |
| 2008/0195422 A1* | 8/2008 | Nessinger et al. | 705/3 |
| 2008/0250323 A1* | 10/2008 | Huff | 715/733 |

* cited by examiner

SYSTEM AND METHOD FOR PROVIDING HEALTHCARE PROGRAM SERVICE BASED ON VITAL SIGNALS AND CONDITION INFORMATION

CLAIM OF PRIORITY

This application claims the benefit of the earlier filing date, under 35 U.S.C. §119(a), to that patent application filed in the Korean Intellectual Property Office on Sep. 11, 2007 and assigned Serial No. 2007-92081, the disclosures of which are incorporated herein by reference.

BACKGROUND OF THE INVENTION

1. Field of the Invention

The present invention relates to the field of wireless communication and networks and generally to a healthcare program service provided through a wireless communication network using the Internet and/or portable terminals, and in particular, to a system and method for providing a healthcare program service based on vital signals and condition information.

2. Description of the Related Art

Generally, to have the benefit of a medical service, a patient must visit the hospital or the public heath center offering the medical service in person. However, the rapid progress of the network technology has facilitated the supply of various Internet-based healthcare system services, allowing the patient to easily check his/her health condition. Regarding the conventional healthcare system, Korean Patent Application No. 10-2003-0008295, entitled 'Internet-Based Healthcare System and Method thereof', discloses a technology of receiving a variety of vital information, such as Heart Rate Variability (HRV), vital warmth, blood sugar level, and body fat scale, over the Internet, diagnosing the health condition in real time depending on the received vital information, and transmitting the results back to the user over the Internet, thereby allowing the user to manage his/her own health condition. However, this technology is a mere technology of gathering vital information and diagnosing the health condition depending thereon. In addition, Korean Patent Registration No. 10-072770, entitled 'System and Method for Providing Health Food Prescription Information through Healthcare', and Korean Patent Application No. 10-2000-0041126, entitled 'Health Diagnosis over Internet and Food Marketing Service Method Based thereon', disclose a technology of receiving a user's vital information measurement data over the network, and recommending prescription information for the health food associated with the vital information measurement data, or recommending appropriate foods to sell them.

However, the above-stated technologies are merely based on a fragmentary functional scheme other than the personalized service where the information of each individual is separately taken into account. Therefore, there is a demand for a learning-based healthcare program recommendation service in which the user's experience information is reflected.

In this context, along with the popularization of Ubiquitous Health (U-Health) in which prevention, diagnosis, treatment, after-service, and healthcare service are available anytime, and anyplace by connecting the information communication to healthcare programs for various diseases, such as stress, hypertension, glycosuria, etc., have recently been developed, and are expected to be provided over the Internet and/or portable terminals. In addition, it is expected that various programs will be provided by enterprises and web sites supporting their care programs for specific diseases.

Therefore, when U-Health is more popularized, the user enjoying the healthcare programs in the on-line environment is expected to face the problem that the user must select, in person, the healthcare program most suitable from among the various healthcare programs provided. As a solution to this problem, there is a scheme in which the web site supporting healthcare programs summarizes the information to the users and delivers the summarized contents to the users so that the users may select the trustable healthcare programs in person. However, this approach, as it provides the same information to all users, has a restriction on its capability, given that the information of a healthcare method effective to other persons may not necessarily be appropriate to the corresponding user.

To address the restriction, therefore, there is a long demand for a scheme for recommending the healthcare program expected to be most proper to the disease of an individual based on vital signals and condition information of the individual

SUMMARY OF THE INVENTION

An aspect of the present invention is to provide a system and method for providing a healthcare program service based on vital signals and condition information, capable of searching for preferred healthcare programs by grouping users having vital signals for similar condition, and databasing the search results to recommend the healthcare program most suitable for a particular user.

According to another aspect of the present invention, there is provided a method for providing a healthcare program service in a system for providing a healthcare service over a wireless communication network. The method includes receiving vital signals for condition, measured by means of corresponding measurement devices, transmitted from multiple users over the wireless communication network, and grouping the received receiving vital signals of symptoms according to particular condition; registering, by a plurality of service providers, corresponding healthcare programs classified by particular diseases, and providing a healthcare program service to the multiple users; receiving a feedback of satisfaction for each of the healthcare programs from each user by means of the corresponding measurement devices, and gathering satisfaction information for the healthcare programs, counting the number of uses for each of the healthcare programs, and determining utilization from said count of the number of users using each of the healthcare programs, adding up the gathered user satisfactions and utilizations, and databasing the results according to preferred healthcare programs of the corresponding user group having vital signals for particular condition; upon receipt of vital signals for condition from a particular user, comparing a similarity of the vital signals for condition of the particular user using the collected healthcare programs; and recommending a preferred healthcare program for a corresponding user group having vital signals for condition, which are most similar to the vital signals for the particular condition, according to the comparison result.

According to another aspect of the present invention, there is provided a system for providing a healthcare program service in a system for providing a healthcare service over a wireless communication network. The system includes a classification unit for receiving vital signals of condition, measured by means of corresponding measurement devices, from multiple users over the wireless communication network, and grouping the received vital signals of condition according to particular condition, a monitoring unit for gathering satisfaction and utilization information of a used healthcare program for each group classified by the vital signals of particular condition and a database for databasing a preferred healthcare program for each user using the gathered utilization and satisfaction information.

BRIEF DESCRIPTION OF THE DRAWINGS

The above and other aspects, features and advantages of the present invention will become more apparent from the following detailed description when taken in conjunction with the accompanying drawings in which.

DETAILED DESCRIPTION OF THE INVENTION

Embodiments of the present invention will now be described in detail with reference to the annexed drawings. The matters defined in the description, such as a detailed construction and elements, are provided to assist in a comprehensive understanding of exemplary embodiments of the invention. Accordingly, those of ordinary skill in the art will recognize that various changes and modifications of the embodiment described herein can be made without departing from the scope and spirit of the invention.

The personalized healthcare program recommendation method disclosed by the present invention can be regarded as a learning-based healthcare program method, as it learns the reactions and effects of the users who have used the healthcare programs, and recommends a proper healthcare program for a new user based on this learning. Further, the proposed effective healthcare programs, which are frequently used in association with the user's vital signals and condition, are updated using the feedback information accumulated through collection of user satisfaction and utilization information. That is, the proposed method classifies users according to their vital signals and condition, and then collections information regarding healthcare program use patterns and results of the users and classified user groups.

Figure 1:
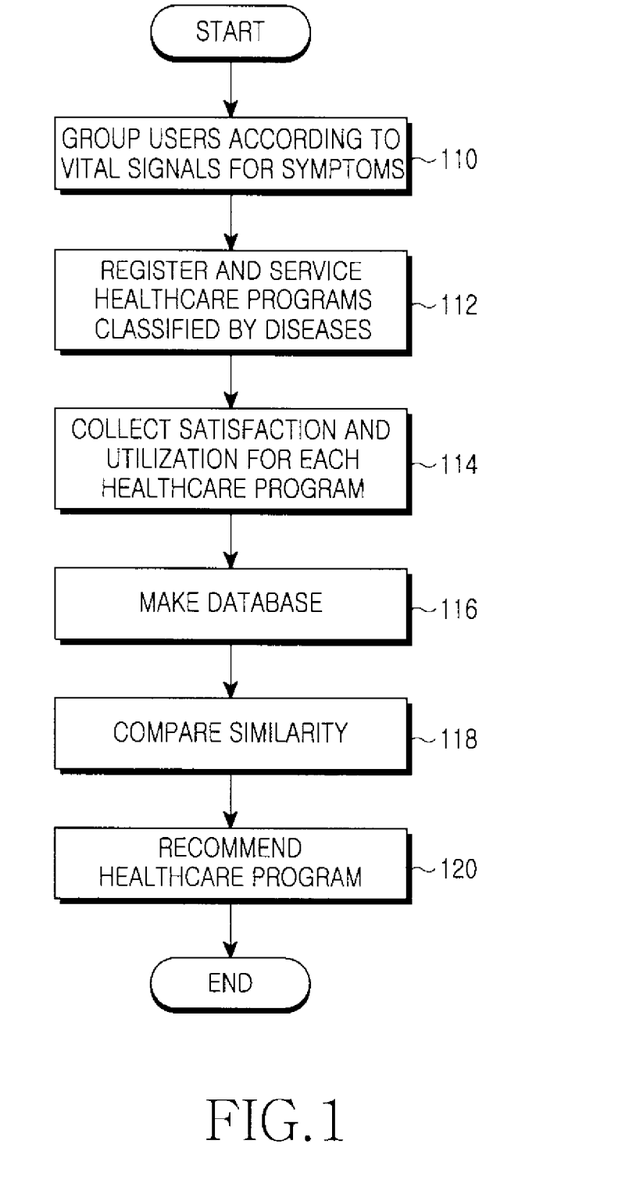
FIG. 1 is a flowchart illustrating a healthcare program service method based on vital signals and condition information according to an embodiment of the present invention.

FIG. 1 is a flowchart illustrating a healthcare program service method based on vital signals and condition information according to an embodiment of the present invention. Referring to FIG. 1, in step 110, in order to classify or group users according to their vital signals of particular condition, vital signals, such as HRV, vital warmth, blood sugar level and body fat scale, for example, associated with condition, such as headache, dyspepsia, skin trouble, breast pressure, nervosity and forgetfulness, for example, are measured by multiple corresponding measurement devices associated with individual users. The condition and vital signals measured in this way are mere examples, and their types are subject to change according to particular diseases and/or the healthcare program service providers.

The measurement device determines in step 110 types $V\{v1, v2, \ldots vn\}$ of available vital signals and types $S=\{s1, s2, \ldots sm\}$ of condition according to particular diseases and service providers, and classifies the vital signals and condition measured by the corresponding measurement devices according to their levels on a level-by-level basis. For example, the measurement device may classify a vital warmth vk into 'High', 'Medium' and 'Low', or may classify it into 'High', 'Medium-High' 'Medium', 'Medium-Low', and 'Low'. The condition can also be classified in the same manner.

After determining the types and levels of the vital signals and condition, the measurement device expresses, as $Pi=(Vi, Si)$, a particular user, Pi, having vital signals $Vi=\{v1,i(1), v2,i(2), \ldots vn,i(n)\}$ and condition $Si=\{s1,i(1), s2,i(2), \ldots sm,i(m)\}$. Note that $i(1)$ is a classification.

After the measurement devices measure vital signals and condition, the measurement devices transmit vital signals and condition to the healthcare program service system over a wireless communication network, and the healthcare program service system groups the transmitted vital signals of condition for each user according to their similarity (Step 110). By means of the grouping, the healthcare program service system can recommend, for a user, a healthcare program for a vital signal group for similar condition and a healthcare program for a similar group corresponding to vital signals for condition for an arbitrary user.

Meanwhile, the measurement devices can acquire the vital signals associated with condition through vital signal detection sensors attached to a part(s) of the user body.

After grouping the vital signals for particular condition, the device transmits the vital signals to the healthcare program service system in step 110, Some experts or developers register healthcare programs for relevant diseases to the healthcare program service system such as one or more network sites capable of supporting the service and/or the web site supporting a service for portable terminals in step 112. Although various schemes for servicing the registered healthcare programs to the users can be provided by the service sites or providers, the user can easily select and access the various services provided.

In step 114, the healthcare program service system receives feedbacks regarding use satisfaction of each healthcare program from each user, by gathering information regarding the satisfaction of the use of a corresponding healthcare program. The service further counts the number of uses for each healthcare program and determines information of utilization of the healthcare programs.

Of course, the utilization and satisfaction information gathered in step 114 is associated with the vital signal and condition information (Vi, Si) of each user Pi. This information is differentiated from the user utilization and satisfaction information generally acquired on the Internet. That is, for the user utilization and satisfaction information collected in step 114, the healthcare program service system can acquire information on the healthcare program preference and utilization of a particular user having particular vital signals and condition.

In step 116, the healthcare program service system creates a database using the healthcare program utilization and satisfaction information associated with the vital signals and condition, acquired in step 114, and stores the information therein.

That is, in the process of creating a database, the healthcare program service system calculates a similarity of elements between the groups having particular condition and vital signals for the particular condition, i.e., similarity of the vital signals of condition, sorts and groups the results, and then sets up a healthcare program list associated with each group.

The operation performed in step 116 is divided herein into two processes: an initialization/classification/database process and a learning-based update process. The initialization/classification/databasing process is achieved by receiving vital signals and condition information from multiple users, (for example, the users may input this information themselves), classifying users having similar information into one group, specifying the classified group as a corresponding group based on the corresponding vital signals and condition information, receiving, from users of each group, use feedback information for multiple healthcare programs, and sorting a healthcare program list suitable for each group based on the feedback information.

The learning-based update process updates the database information, when a particular user requires recommendation of healthcare programs, compares (checks) a similarity between vital signals for condition of the particular user and vital signals for condition associated with a group, and recommends a corresponding healthcare program list for the group.

Therefore, as to the process of step 116, in an initial embodiment of the present invention, the databasing process is performed using the feedback information of the healthcare program, which is collected from multiple users, and as a large amount of information is accumulated due to the databasing process, the process of step 116 enables reliable healthcare program recommendation for an arbitrary user associated with each group.

In this manner, the healthcare program service system of the present invention can provide a database evolved from the database in the initial embodiment, as the greater amount of information from the multiple users is accumulated, and the healthcare programs are updated based on the accumulated information, e.g., user satisfaction and utilization. After performing the databasing process in step 116, if a condition and vital signals for the condition are transmitted from a particular user, the healthcare program service system performs a similarity comparison process for recommendation of the healthcare program corresponding to the vital signals for the condition (Step 118).

More specifically, in order to search for a healthcare program suitable for a user Pi having vital signals Vi={v1,$i$(1), v2,$i$(2), ... vn,i(n)} and condition Si={s1,$i$(1), S2,$i$(2), ..., Sm,i(m)}, the healthcare program service system searches for a group having the highest similarity of vital signals and condition information Pi=(Vi, Si) for the user Pi. The healthcare program service system makes a search for a similarity of elements between the groups, Pj, and vital signals of condition for the user Pi, using Equation (1) and Equation (2).

$$\text{diff\_of\_condition}(Pi,Pj)=\{|s1,i[1]-s1,j[1]|, \ldots, |s1,i[m]-s1,j[m]|\} \quad (1)$$

$$\text{diff\_of\_vital\_sign}(Pi,Pj)=\{|v1,i[1]-v1,j[1]|, \ldots, |v1,i[n]-v1,j[n]|\} \quad (2)$$

where diff_of_condition means a difference of condition, and diff_of_vital_sign means a difference of vital signals.

Using the differences of vital signals for condition between from Equation (1) and Equation (2), the healthcare program service system using inner products of predetermined vital signal weight vector, weight_vector(vital_sign), and condition weight vector, weight_vector(condition), derives a sum of the differences to calculate a similarity value between the two subjects. That is, Equation (3) for deriving a similarity value between two subjects Pi and Pj is used for calculating the similarity value.

$$\text{Similarity\_Score}(Pi, Pj) = \qquad (3)$$

$$C1 \cdot \sum_{K=1}^{k} \text{diff\_of\_vital\_sign}_k(P_i, P_j) \cdot \text{weight\_vector}_k +$$

$$C2 \cdot \sum_{m=1}^{i} \text{diff\_of\_condition}_m(P_i, P_j) \cdot \text{weight\_vector}_k(\text{condition})$$

where c1 and c2 are constants determined according to relative weights applied to the vital signal and condition.

Therefore, c1 and c2 are values which are subject to change according to the types of the vital signals or classified diseases or condition. The similarity value derived by Equation (3) is large for a low similarity between the two subjects, and is small for a large similarity. Therefore, the similarity value between vital signals for the same signals and/or condition is 0.

Figure 2:
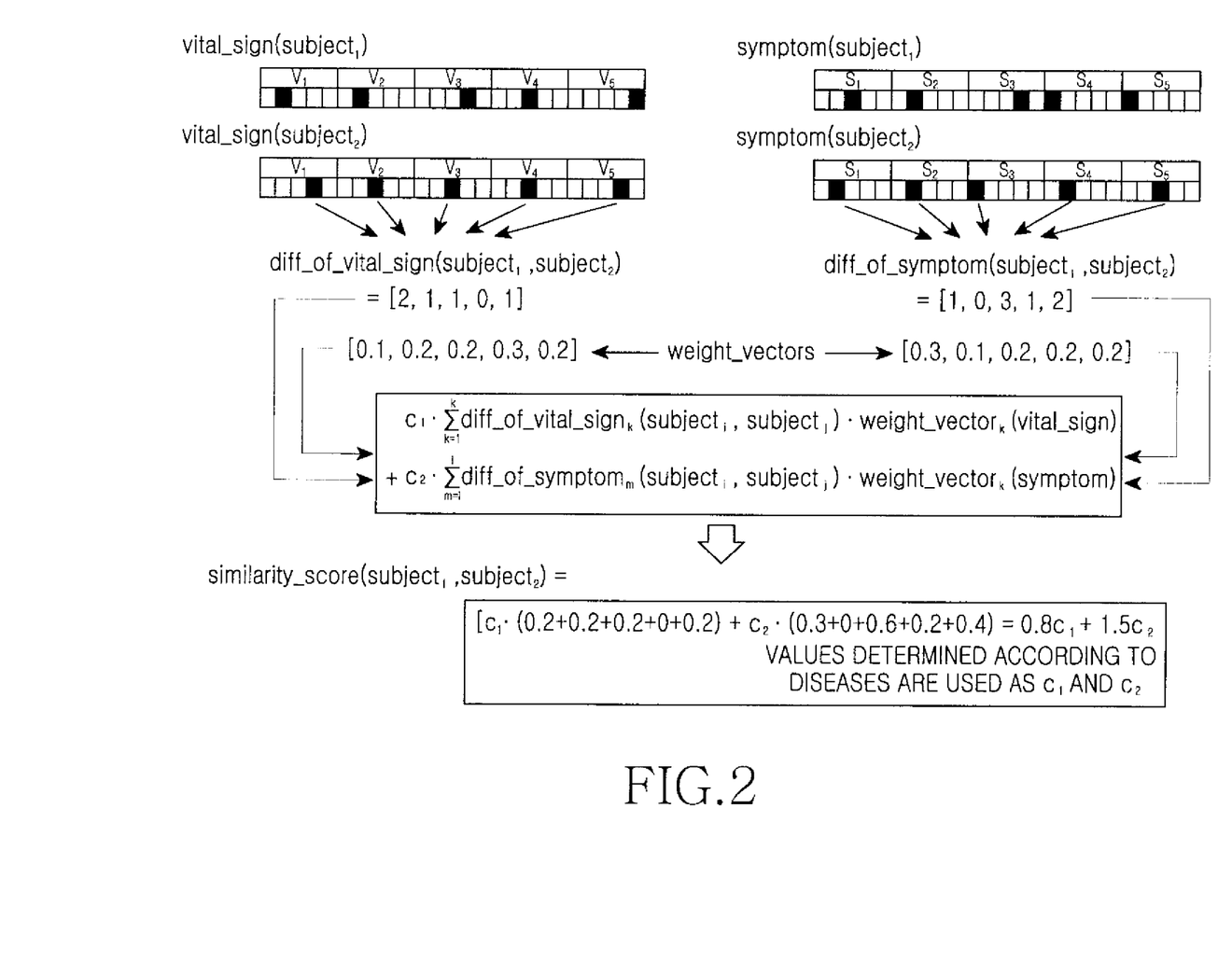
FIG. 2 is a diagram schematically illustrating a calculation process performed in the similarity comparison process between two persons according to an embodiment of the present invention.

FIG. 2 schematically illustrates a calculation process performed in the similarity comparison process between two subjects.

Referring to FIG. 2, in the situation where 5 vital signals and condition are both classified into 5 levels in the same way, and when vital signals and condition for two given subjects are given, the healthcare program service system calculates level differences between the two subjects and performs similarity check by applying the signals and condition of the subjects to Equation (3) using predetermined weight vectors.

Returning to FIG. 1, the healthcare program service system provides a healthcare program list associated with the group in which the similarity value converges to zero (0), determined in step 118, and makes a recommendation of the highest-priority healthcare program in the healthcare program list (Step 120).

The recommendation of a highest-priority healthcare program is based on a healthcare program list in which utilization and satisfaction associated with the selected group having the most similar condition to those of a particular user belongs, are sorted in highest-priority order.

Figure 3:
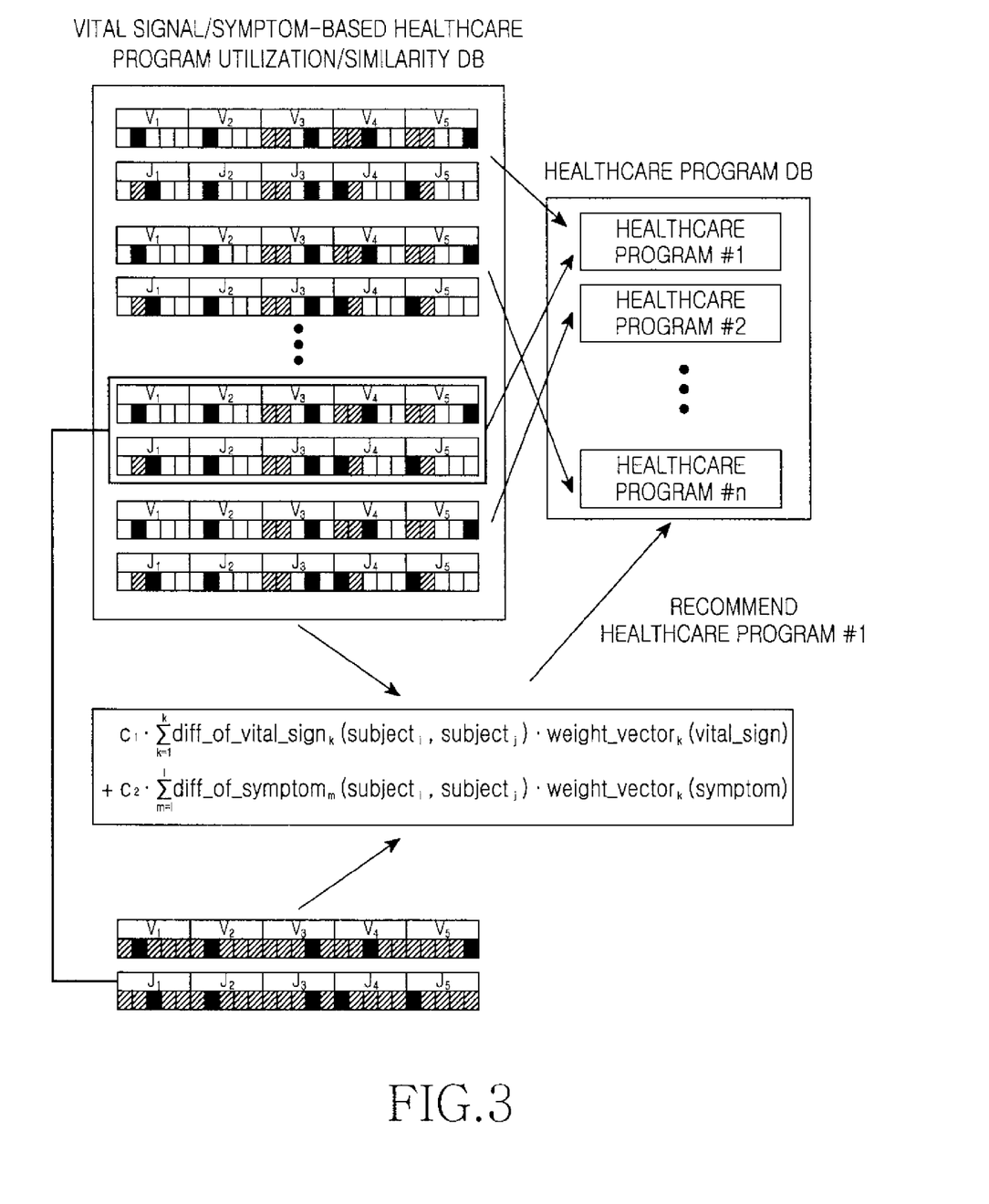
FIG. 3 is a diagram schematically illustrating a calculation process performed in the process of recommending a healthcare program according to an embodiment of the present invention.

The calculation process performed in the healthcare program recommendation process in step 118 is shown in FIG. 3.

Figure 4:
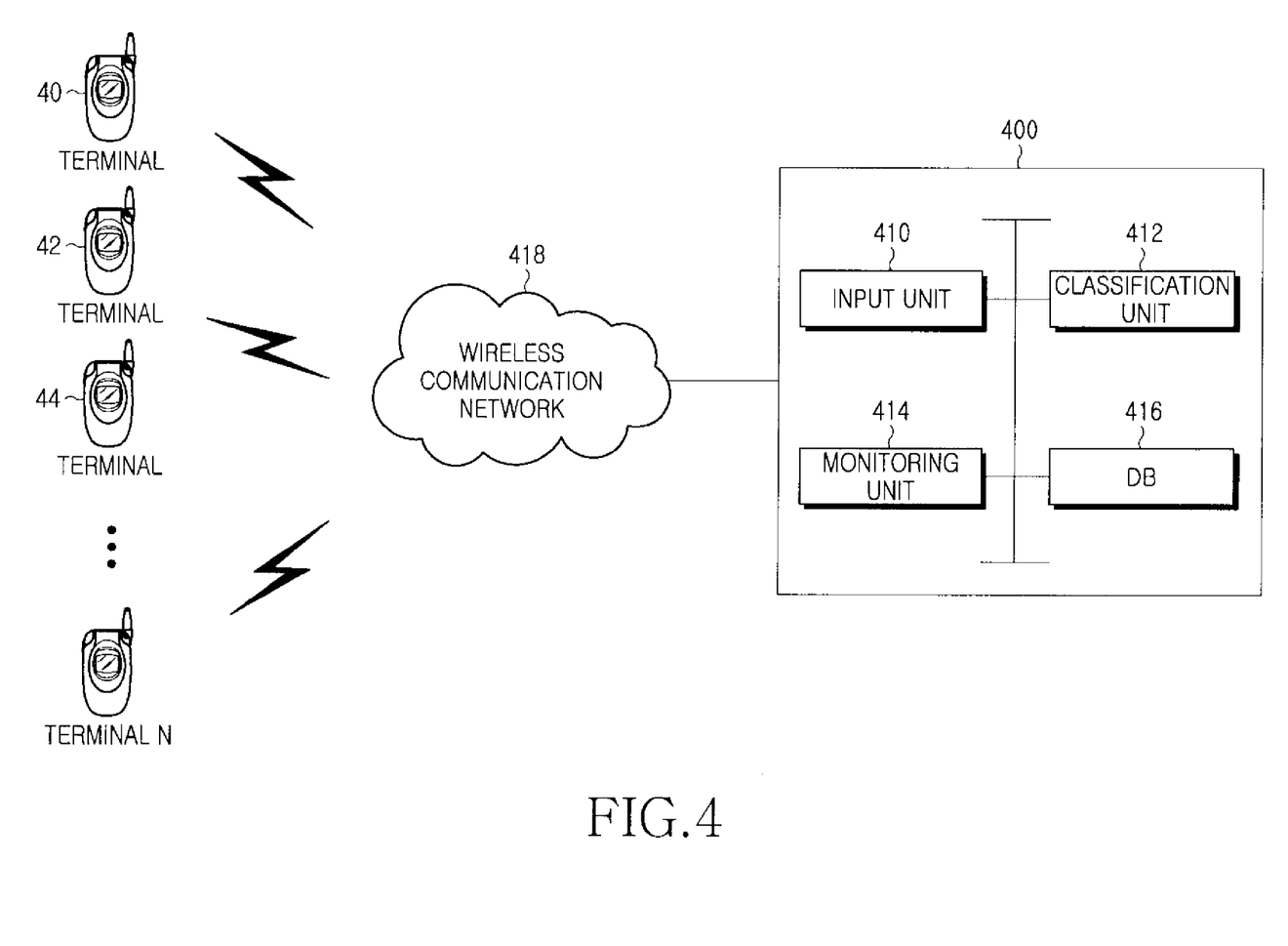
FIG. 4 is a diagram illustrating a network configuration where the healthcare program service based on vital signals and condition information is achieved according to an embodiment of the present invention.

A detailed description will now be made of the system for providing the healthcare program service using the healthcare program service method based on the vital signals and condition information according to an embodiment of the present invention. FIG. 4 is a diagram illustrating a network configuration where the healthcare program service based on vital signals and condition information is achieved according to an embodiment of the present invention. Referring to FIG. 4, the network configuration includes a wireless communication network 418, a healthcare program service system 400, and a plurality of portable terminals 40, 42, 44 ..., n.

The wireless communication network 418, an integrated network for safely providing mobile communication services, enables a user to enjoy all of the communication, broadcast and Internet with one portable terminal, and for the healthcare program service, it is used for forwarding data between the healthcare program service system 400 and the multiple portable terminals 40, 42, 44, ..., n.

The healthcare program service system 400 is adapted to provide the most suitable and trustable healthcare program based on the vital signals for condition corresponding to the healthcare program service user.

The portable terminals 40, 42, . . . , n are portable terminals with which the users enjoy the healthcare program recommended by the present invention, and each portable terminal must include sensors that can be attached to a part(s) of the user body or can receive information from sensors attached to the body, to detect vital signals of the user and measure strength of the vital signals, for example. For convenience' sake, reference will be made herein only one of the multiple portable terminals 40, 42, . . . , n, but the same operation is applied to the portable terminals 40, 42, . . . , n.

The portable terminal 40 acquires vital signals of a corresponding user by means of a vital signal detection sensor (not shown) and condition inputted by the user, and then transmits the acquired vital signals for condition to the healthcare program service system 400 over the wireless communication network 418.

The healthcare program service system 400, as shown in FIG. 4, includes an input unit 410, a classification unit 412, a monitoring unit 414, and a database (DB) 416.

The input unit 410 receives a condition and vital signals for the condition of multiple users, transmitted over the wireless communication network 418. The classification unit 412 classifies the vital signals for condition by separately grouping the received vital signals for condition of users according to particular condition. Here, the classified groups can be used to select a preferred healthcare program.

The monitoring unit 414 gathers satisfaction data associated with the healthcare programs of each group, grouped according to the vital signals for particular condition, and gathers utilization of the healthcare programs by counting the number of uses of the healthcare programs.

The utilization and satisfaction information gathered by the monitoring unit 414 is associated with vital signal information (Vi, Si) for condition of a user Pi. This information is differentiated from the user utilization and satisfaction information generally acquired on the Internet. That is, the user utilization and satisfaction information collected by the monitoring unit 414 can be information on the healthcare program preference and utilization of a particular user having particular vital signals and condition.

The database module 416 creates a database using the utilization and satisfaction information of healthcare programs associated with the vital signals for condition, acquired by the monitoring unit 414, and stores the information within the database. A detailed structure of the database 416 will be described with reference to FIG. 5.

Figure 5:
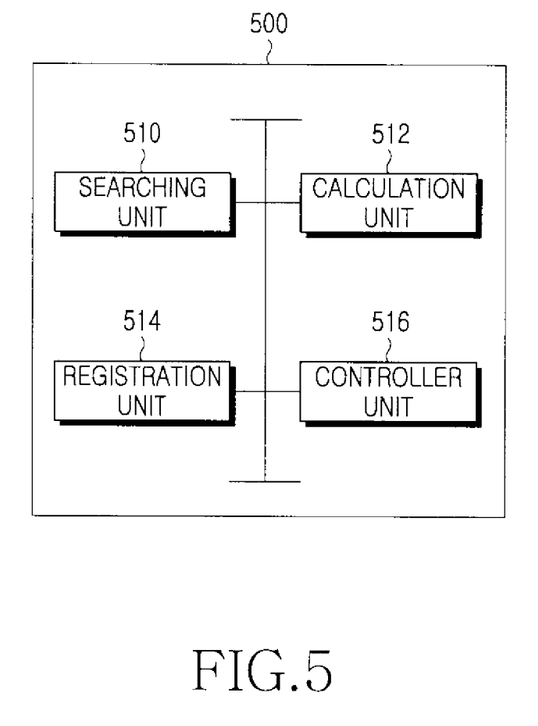
FIG. 5 is a block diagram illustrating a database in a healthcare program service system based on vital signals and condition information according to an embodiment of the present invention.

FIG. 5 is a detailed block diagram illustrating a database module in a healthcare program service system based on vital signals and condition information according to an embodiment of the present invention.

As illustrated in FIG. 5, a database module 500 includes a searching unit 510, a calculation unit 512, a registration unit 514, and a controller 516.

Herein, the database module 500 according to the present invention performs two operations: an initialization/classification/databasing operation and a learning-based update operation.

In the initialization process, as the input unit 410 receives vital signals and condition information, which the user may input by filling out a questionnaire stored in portable terminals, from multiple users and the classification unit 412 classifies users having similar information into one group, the database module 500 specifies the classified group as a corresponding group based on the corresponding vital signals and condition information, receives, from users of each group, use feedback information regarding for multiple healthcare programs supported over the wireless communication network, and sorts a healthcare program list suitable for each group based on the feedback information.

In the learning-based update process, when a particular user requires a recommendation of healthcare programs, the database module 500 checks a similarity between vital signals for condition, sorts similar groups, and creates healthcare program list of the similar group.

Therefore, upon receipt of vital signals for corresponding condition from a particular user, the searching unit 510 searches for a group indicating vital signals for condition, which are similar to the received vital signals for condition of the user.

Accordingly, in order to detect a similarity of vital signals for condition of an arbitrary user in the group, the calculation unit 512 employs predefined Equations (1) and (2), and applies the values acquired therefrom to Equation (3) to calculate a similarity value between two subjects, The calculated similarity value is large for a low similarity between the two users, and is small for a high similarity. Therefore, the similarity value between vital signals for the same condition is 0.

The controller 516 recommends a healthcare program to the user corresponding to vital signals for particular condition according to the similarity value calculated by the calculation unit 512, and updates the healthcare program service according to the accumulated feedback information of the recommended healthcare program. Therefore, the update operation is performed as the amount of accumulated feedback information from the multiple users increases, i.e., as the number of multiple users using the corresponding service increases.

In the initialization process of the healthcare program service system 400, the registration unit 514 registers healthcare programs, classified by diseases, at sites capable of supporting the service and/or the web sites supporting the service for portable terminals.

As is apparent from the foregoing description, the present invention can provide a priority-based recommended list of personalized healthcare programs expected to be suitable using vital signals of condition of a particular person in the on-line environment where various healthcare programs classified by diseases are provided.

The above-described methods according to the present invention can be realized in hardware or as software or computer code that can be stored in a recording medium such as a CD ROM, an RAM, a floppy disk, a hard disk, or a magneto-optical disk or downloaded over a network, so that the methods described herein can be rendered in such software using a general purpose computer, or a special processor or in programmable or dedicated hardware, such as an ASIC or FPGA. As would be understood in the art, the computer, the processor or the programmable hardware include memory components, e.g., RAM, ROM, Flash, etc. that may store or receive software or computer code that when accessed and executed by the computer, processor or hardware implement the processing methods described herein.

While the invention has been shown and described with reference to a certain preferred embodiment thereof it will be understood by those skilled in the art that various changes in form and details may be made therein without departing from the spirit and scope of the invention as defined by the appended claims.

What is claimed is:

1. A method for providing a healthcare program service in a system for providing a healthcare service over a wireless communication network, the method comprising:

receiving measured vital signals associated with a condition, measured by means of corresponding measurement devices, transmitted from multiple users over the wireless communication network, and generating a grouping of the received measured vital signals according to a particular condition;

registering corresponding healthcare programs classified by particular diseases, receiving a feedback for a use satisfaction for each of the healthcare programs from each user by means of the corresponding measurement devices, and gathering information associated with a satisfaction for each of the healthcare programs;

counting the number of uses of a healthcare service for each of the healthcare programs, and determining utilization for each of the healthcare programs based on the number of uses;

searching for a corresponding group of users using each of the healthcare programs, adding up the gathered user satisfactions and utilizations, and databasing the results according to preferred healthcare programs of the corresponding user group;

upon receipt of measured vital signals from a particular user, applying weights to the measured vital signals to generate a similarity value, and comparing the similarity value of the measured vital signals of the particular user to the generated grouping of previously received measured vital signals using the databased healthcare programs to generate a comparison result;

recommending a preferred healthcare program for a corresponding user group having vital signals for a condition, which is most similar to the received measured vital signals for the particular user, according to the comparison result;

receiving a feedback information for the use satisfaction of the recommended healthcare program from the particular user;

generating and providing a healthcare program recommendation list of healthcare programs sorted based on the feedback information; and updating the recommended healthcare program according to the feedback information of the recommended healthcare program.

2. The method of claim 1, wherein types of the vital signals for the condition are subject to change according to diseases or provided services.

3. The method of claim 1, wherein the vital signals for the condition of each of the users comprise a set of at least two vital signals and a combination of the condition, the number of which is equal to the number of vital signals corresponding to the combination of the at least two vital signals.

4. The method of claim 1, wherein the vital signals for the condition are classified according to their strength measured by the corresponding measurement devices on a level-by-level basis.

5. The method of claim 1, wherein the user satisfactions and utilizations are associated with vital signals for the condition of each user for each healthcare program.

6. The method of claim 1, wherein comparing the similarity value comprises:

searching for a group having vital signals for the condition, which most highly converge onto vital signal information for condition of a particular user Pi having a combination of at least two vital signals and a combination of the condition;

checking differences of vital signals and the condition between users Pj and Pi by applying vital signal information for the condition of the user Pj belonging to the searched group and vital signal information for condition of the user Pi to the following Equations (1) and (2), respectively;

$$\text{diff\_of\_condition}(Pi,Pj) = \{|s1,i[1]-s1,j[1]|, \ldots, |s1,i[m]-s1,j[m]|\} \quad (1)$$

$$\text{diff\_of\_vital\_sign}(Pi,Pj) = \{|v1,i[1]-v1,j[1]|, \ldots, |v1,i[n]-v1,j[n]|\} \quad (2)$$

where diff_of_condition denotes a difference of condition, and diff_of_vital_sign denotes a difference of vital signals; and acquiring differences of vital signals and the condition between Pj and Pi from Equations (1) and (2), calculating inner products of weight vectors indicating the weights of the vital signal and condition of each user using the acquired differences, deriving a sum of the differences as:

$$\text{Similarity\_Score}(Pi, Pj) = \\ C1 \cdot \sum_{k=1}^{k} \text{diff\_of\_vital\_sign}_k(P_i, P_j) \cdot \text{weight\_vector}_k + \\ C2 \cdot \sum_{m=1}^{l} \text{diff\_of\_condition}_m(P_i, P_j) \cdot \text{weight\_vector}_k(\text{condition}) \quad (3)$$

wherein c1 and c2 are constants determined according to relative weights applied to the vital signal and the condition.

7. The method of claim 6, wherein the weight vectors are predetermined.

8. The method of claim 6, wherein the similarity value derived from Equation (3) is large for a low similarity between Pj and Pi, and is small for a high similarity between Pj and Pi.

9. The method of claim 6, wherein the similarity value between users having vital signals for the same condition is zero (0).

10. The method of claim 1, wherein the healthcare program recommendation list is sorted in a highest-priority order.

11. A non-transitory recording medium readable in a computer, in which a program for executing the method is recorded thereon, the program when accessed by a processor causes the processor to execute the steps of:

receiving measured vital signals associated with a condition, measured by means of corresponding measurement devices, transmitted from multiple users over the wireless communication network, and generating a grouping of the received measured vital signals according to a particular condition;

registering corresponding healthcare programs classified by particular diseases, receiving a feedback for a use satisfaction for each of the healthcare programs from each user by means of the corresponding measurement devices, and gathering information associated with a satisfaction for each of the healthcare programs;

counting the number of uses of a healthcare service for each of the healthcare programs, and determining utilization for each of the healthcare programs based on the number of uses;

searching for a corresponding group of users using each of the healthcare programs, adding up the gathered user satisfactions and utilizations, and databasing the results according to preferred healthcare programs of the corresponding user group;

upon receipt of measured vital signals from a particular user, applying weights to the measured vital signals to generate a similarity value, and comparing the similarity value of the measured vital signals of the particular user to the generated grouping of previously received measured vital signals using the databased healthcare programs to generate a comparison result;

recommending a preferred healthcare program for a corresponding user group having vital signals for a condition, which is most similar to the received measured vital signals for the particular user, according to the comparison result;

receiving a feedback information for the use satisfaction of the recommended healthcare program from the particular user;

providing a healthcare program recommendation list of healthcare programs sorted based on the feedback information; and updating the recommend healthcare program according to the feedback information of the recommended healthcare program.

12. An electronic system for providing a healthcare program service in a system for providing a healthcare service over a wireless communication network, the electronic system comprising:

a classification unit including a processor for receiving measured vital signals for a condition, measured by means of corresponding measurement devices, from multiple users over the wireless communication network, and generating a grouping of the received measured vital signals for a condition according to a particular condition;

a monitoring unit for gathering satisfaction and utilization information of a used healthcare program for each group classified by the measured vital signals for the particular condition; and an electronic database for collecting information regarding each healthcare program for each user using the gathered utilization and satisfaction information, wherein, when the classification unit receives measured vital signals from a particular user, the electronic database applies weights to the measured vital signals to generate a similarity value, and compares the similarity value of the vital signals of the particular user to the generated grouping of previously received measured vital signals using the databased healthcare programs to generate a comparison result, recommends a preferred healthcare program for a corresponding user group having vital signals for a condition, which is most similar to the received measured vital signals for the particular user, according to the comparison result, receives feedback information for the use satisfaction of the recommended healthcare program from the particular user, generates and provides a healthcare program recommendation list of healthcare programs sorted based on the feedback information, and updates the recommend healthcare program according to the feedback information of the recommended healthcare program.

13. The electronic system of claim 12, wherein the database comprises:

a registration unit for registering a plurality of healthcare programs classified by diseases at a site capable of supporting a service or a web site supporting a service for a portable terminal;

a searching unit for searching for a group classified by vital signals for the condition which are similar to the vital signals for the corresponding condition are received from a particular user Pi;

a calculation unit for determining differences of vital signals for the condition between users Pi and Pj by applying a similarity to vital signals for the condition of an arbitrary user Pj in the searched group as;

$$\text{diff\_of\_condition}(Pi,Pj) = \{|s1,i[1]-s1,j[1]|, \ldots, |s1,i[m]-s1,j[m]|\} \quad (1)$$

$$\text{diff\_of\_vital\_sign}(Pi,Pj) = \{|v1,i[1]-v1,j[1]|, \ldots, |v1,i[n]-v1,j[n]|\} \quad (2)$$

where diff_of_condition denotes a difference of the condition, and diff_of_vital_sign denotes a difference of vital signals; and calculating the similarity value between users Pi and Pj by applying the weights to the acquired difference of vital signals for the condition between Pi and Pj as:

$$\text{Similarity\_Score}(Pi, Pj) = \qquad (3)$$

$$C1 \cdot \sum_{K=1}^{k} \text{diff\_of\_vital\_sign}_k(P_i, P_j) \cdot \text{weight\_vector}_k +$$

$$C2 \cdot \sum_{m=1}^{l} \text{diff\_of\_condition}_m(P_i, P_j) \cdot \text{weight\_vector}_k(\text{condition});$$

where c1 and c2 are constants determined according to relative weights applied to the vital signal and the condition; and a controller for recommending the recommended healthcare program to the particular user corresponding according to the similarity value calculated by the calculation unit, and making an update according to the feedback information for the recommended healthcare program.

14. The electronic system of claim 12, wherein the vital signals for the condition of each of the users is a set of at least two vital signals and a combination of the condition, the number of which is equal to the number of vital signals corresponding to the combination of the at least two vital signals.

15. A portable terminal for providing vital signal information via a wireless communication network, said portable terminal comprising:

a sensor receiving unit for receiving measured vital signal information from corresponding sensor units measuring vital signals of a particular user;

a transceiver unit for transmitting and receiving information via said wireless communication network;

wherein the transceiver unit transmits the received measured vital signal information to an electronic system;

wherein the transceiver unit receives recommendation information for output to the particular user, with the recommendation information generated by the electronic system by:

processing received measured vital signals associated with a condition transmitted from multiple users over the wireless communication network;

generating a grouping of the received measured vital signals according to a particular condition;

upon receipt of measured vital signals from the particular user, applying weights to the measured vital signals to generate a similarity value, and comparing the similarity value of the measured vital signals of the particular user to the generated grouping of previously received measured vital signals using the data-based healthcare programs to generate a comparison result; and generating the recommendation information recommending a preferred healthcare program for a corresponding user group having vital signals for a condition, which is most similar to the received measured vital signals for the particular user, according to the comparison result; and an output device for outputting the recommendation information, and for generating and providing a healthcare program recommendation list of healthcare programs sorted based on feedback information.

16. The portable terminal of claim 15, wherein said corresponding sensor units are included within said portable terminal.

17. The portable terminal of claim 15 further comprising: a short-range communication receiver.

18. The portable terminal of claim 15, wherein said corresponding sensor units are separated from said portable terminal and in communication with said portable terminal via said short-range communication receiver.

19. The non-transitory recording medium of claim 11, wherein the healthcare program recommendation list is sorted in a highest-priority order.

20. The electronic system of claim 12, wherein the electronic database provides the healthcare program recommendation list sorted in a highest-priority order.

* * * * *